US009371365B2

(12) United States Patent
Lambris et al.

(10) Patent No.: US 9,371,365 B2
(45) Date of Patent: *Jun. 21, 2016

(54) MODIFIED COMPSTATIN WITH PEPTIDE BACKBONE AND C-TERMINAL MODIFICATIONS

(71) Applicant: The Trustees of the University of Pennsylvania, Philadelphia, PA (US)

(72) Inventors: John D. Lambris, Philadelphia, PA (US); Hongchang Qu, Torrance, CA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/611,742

(22) Filed: Feb. 2, 2015

(65) Prior Publication Data
US 2015/0203539 A1 Jul. 23, 2015

Related U.S. Application Data

(63) Continuation of application No. 13/318,272, filed as application No. PCT/US2010/033345 on May 3, 2010, now Pat. No. 8,946,145.

(60) Provisional application No. 61/339,458, filed on Mar. 4, 2010, provisional application No. 61/174,575, filed on May 1, 2009.

(51) Int. Cl.
| A61K 38/00 | (2006.01) |
| C07K 9/00 | (2006.01) |
| C07K 7/08 | (2006.01) |
| A61K 38/12 | (2006.01) |
| A61K 47/48 | (2006.01) |

(52) U.S. Cl.
CPC ............ *C07K 9/006* (2013.01); *A61K 38/12* (2013.01); *A61K 47/48023* (2013.01); *A61K 47/48246* (2013.01); *C07K 7/08* (2013.01); *A61K 38/00* (2013.01)

(58) Field of Classification Search
None
See application file for complete search history.

(56) References Cited

U.S. PATENT DOCUMENTS

| 4,299,838 | A | 11/1981 | Durlach |
| 4,576,750 | A | 3/1986 | Pitzenberger |
| 4,870,097 | A | 9/1989 | Makovec et al. |
| 5,776,970 | A | 7/1998 | Shechter |
| 6,169,057 | B1 | 1/2001 | Lovatt |
| 6,214,790 | B1 | 4/2001 | Richelson et al. |
| 6,319,897 | B1 | 11/2001 | Lambris |
| 2007/0238654 | A1* | 10/2007 | Deschatelets et al. ......... 514/9 |

FOREIGN PATENT DOCUMENTS

| WO | WO 99/13899 A1 | 3/1999 |
| WO | WO 2004/026328 | * 4/2004 |
| WO | WO 2004/026328 A1 | 4/2004 |
| WO | WO 2007/062249 A2 | 5/2007 |
| WO | WO 2008/153963 A1 | 12/2008 |

OTHER PUBLICATIONS

Wermuth, et al Glossary of Terms Used in Medicinal Chemistry, Pure & Appl. Chem., vol. 70, No. 5, pp. 112-1143 (1998).*
Furlong et al., "C3 activation is inhibited by analogs of compstatin but not by serine protease . . . ", Immunopharmacology, vol. 48, pp. 199-212 (2000).*
Mallick et al,, "Development of a quasi-dynamic pharmacophore model for anti-complement peptide analogues", J. Am. Chem. Soc., vel. 127, pp. 10967-10976 (2005).*
Rajeswaran, W.G., et al, N-Methyl Scan of Somatostatin Octapeptide Agonists Produces Interesting Effects on Receptor Subtype Specificity, J. Med. Chem. 2001, 44, 1416-1421.*
Biron, et al. "Optimized selective N-methylation of peptides on solid support" J. Peptide Sci. vol. 12, pp. 213-219 (2006).
Brooks, et al. "CHARMM: A Program for Macromolecular Energy, Minimization, and Dynamics Calculations" J. Comput. Chem., vol. 4, pp. 187-217 (1983).
Chatterjee, et al. "N-Methylation of Peptides: A New Perspective in Medicinal Chemistry" Acc. Chem. Res., vol. 41, pp. 1331-1342.
Chiu et al., "Development of a New Pharmacophore Model That Discriminates Active Compstatin Analogs" Chem. Biol. Drug Des., vol. 72, pp. 249-256 (2008).
Coleman et al., "Age-related macular degeneration" Lancet, vol. 372, pp. 1835-1845 (2008).
Darden et al., "Particle Mesh Ewald-an N.Log(N) method for Ewald sums in large systems" J. Chem. Phys., vol. 98, pp. 10089-10092 (1993).
Dennis et al,, "Albumin Binding as a General Strategy for Improving the Pharmacokinetics of Proteins" J. Biol. Chem., vol. 277, pp. 35035-35043 (2002).
Feller et al., "Constant pressure molecular dynamics simulation: The Langevin piston method" J. Chem. Phys., vol. 103, pp. 4613-4621 (1995).
Fiane et al., "Compstatin, a peptide inhibotr of C3, prolongs survival of ex vivo perfused pig xenografts" Xenotransplantation, vol. 6, pp. 52-65 (1999).
Fiane et al., "Prolongation of ex vivo perfused pig xenograft survival by the complement inhibotr compstatin" Transplant Proc., vol. 31, pp. 934-935 (1999).
Furlong et al., "C3 activation is inhibited by analogs of compstatin but not by serine protease . . . " Immunopharmacology, vol. 48, pp. 199-212 (2000).
Holers, "The complement system as a therapeutic target in autoimmunity" Clin. Immunol., vol. 107, pp. 140-51 (2003).
Humphrey et al., "VMD: visual molecular dynamics" J. Mol. Graphics, vol. 14, pp. 33-38, 27-28 (1996).

(Continued)

*Primary Examiner* — Thomas S Heard
(74) *Attorney, Agent, or Firm* — Potter Anderson and Corroon LLP

(57) ABSTRACT

Compounds comprising peptides capable of binding C3 protein and inhibiting complement activation are disclosed. These compounds display greatly improved complement activation-inhibitory activity as compared with currently available compounds. The compounds comprise compstatin analogs having a constrained backbone at position 8 (glycine) and, optionally, specific substitutions for threonine at position 13.

19 Claims, No Drawings

(56) References Cited

OTHER PUBLICATIONS

Jannsen et al., "Structure of Compstatin in Complex with Complement Component C3c Reveals a New Mechanism of . . . " J. Biol. Chem., vol. 282, pp. 29241-29247 (2007).

Jorgensen et al., "Comparison of simple potential functions for simulating liquid water" J. Chem. Phys., vol. 79, pp. 926-935 (1983).

Katragadda et al., "Expression of compstatin in *Escherichia coli*: Incorporation of unnatural amino acids . . . " Protein Expr. Purif., vol. 47, pp. 289-295 (2006).

Katragadda et al., "Hydrophobic effect and hydrogen bonds account for the improve . . . " J. Med. Chem., vol. 49, pp. 4616-4622 (2006).

Klepeis et al., Integrated Computational and Experimental Approach for Lead Optimization and Design . . . , J. Am. Chem. Soc., vol. 125, pp. 8422-8423 (2003).

Mackerell et al., "All-Atom Empirical Potential for Molecular Modeling and Dynamics Studies of Proteins" J. Phys. Chem., vol. B102, pp. 3586-3616 (1998).

Mallik et al., "Design and NMR characterization of active analogues of compstatin . . . " J. Med. Chem., vol. 48, pp. 274-286 (2005).

Mallick et al,, "Development of a quasi-dynamic pharmacophore model for anti-complement peptide analogues", J. Am. Chem. Soc., vol. 127, pp. 10967-10976 (2005).

Markiewski et al, "The role of complement in inflammatory diseases from behind the scenes into the spotlight", Am. J. Pathol., vol. 171, pp. 715-727 (2007).

Martyna et al., "constant pressure molecular dynamics algorithms", J. Chem. Phys., vol. 101, pp. 4177-4189 (1994).

Morikis et al., "Solution structure of Compstatin, a potent complement inhibitor", Protein Sci., vol. 7, pp. 619-627 (1998).

Morikis et al., "Structural aspects and design of low-molecular-mass complement inhibitors", Biochem. Soc. Trans., vol. 30, pp. 1026-1036 (2002).

Morikis et al., "The structural basis of compstatin activity examined by structure-function-base . . . ", J. Biol. Chem., vol. 277, pp. 14942-14953 (2002).

Mulakala et al., "A simple, yet highly accurate, QSAR model captures the complement inhibitory activity of compstatin", Bioorg. Med. Chem., vol. '15, pp. 1638-1644 (2007).

Nguyen et al., "The pharmacokinetics of an albumin-binding Fab (AB.Fab) can be modulated as a function of affinity . . . ", Protein Eng. Des. Sel., vol. 19, pp. 291-297(2006).

Nilsson et al., "Compstatin inhibits cellular and complement activation in whole blood in two models of extra corporeal circulation", Blood, vol. 92, pp. 1661-1667 (1998).

Phillips et al., "Scalable molecular dynamics with NAMD", J. Comput. Chem., vol. 26, pp. 1781-1802 (2005).

Rajeswaran et al. "N-methyl scan of somatostatin octapeptide agonists produces interesting effects on receptor subtype specificity" J. Med. Chem. vol. 44, pp. 1416-1421 (2001).

Ricklin et al, "Complement-targeted therapeutics", Nat. Biotechnol., vol, 25, pp. 1265-1275 (2007).

Ricklin et al., "Compstatin: a complement inhibitor on its way to clinical application", Adv. Exp. Med. Biol., vol. 632, pp. 273-292 (2008).

Sahu et al., "Inhibition of human complement by a C3-binding peptide isolated from a phage . . . ", J. Immunol., vol. 157, pp. 884-891 (1996).

Sahu et al., "Binding kinetics, structure-activity relationship, and biotransformation of the complemen . . . ", J. Immunol., vol. 165, pp. 2491-2499 (2000).

Schmidt et al., "Inhibitor of complement, Compstatin, prevents polymer-mediated Mac-1 up-regulation of human.,.", J. Biomed. Mater. Res. A, vol. 66A, pp. 491-499 (2003).

Soulika et al., "Inhibition of heparin/protamine complex-induced complement activation by Compstatin . . . ", Clin. Immunol., vol. 96, pp. 212-221 (2000).

Wermuth et al. "Glossary of Terms Used in Medicinal Chemistry" Pure & Appl. Chem. vol. 70(5), pp. 1129-1143 (1998).

International Search Report in PCT/US2010/033345, mailed Jul. 16, 2010.

Written Opinion of the International Searching Authority in PCT/US2010/033345, mailed Jul. 16, 2010.

International Preliminary Report on Patentability in PCT/US2010/033345, issued Nov. 1, 2011.

Non-final Office Action in U.S. Appl. No. 13/318,272, mailed Dec. 5, 2013.

Final Office Action in U.S. Appl. No. 13/318,272, mailed May 13, 2014.

Notice of Allowance in U.S. Appl. No. 13/318,272, mailed Sep. 17, 2014.

\* cited by examiner

MODIFIED COMPSTATIN WITH PEPTIDE BACKBONE AND C-TERMINAL MODIFICATIONS

CROSS REFERENCE TO RELATED APPLICATIONS

Continuation of U.S. application Ser. No. 13/318,272 filed Sep. 21, 2011, now U.S. Pat. No. 8,946,145, which is a United States national stage application under 35 U.S.C. §371 of International Application No. PCT/US2010/033345, filed May 3, 2010, which claims benefit of U.S. Provisional Application Nos. 61/174,575, filed May 1, 2009, and 61/339,454, filed Mar. 4, 2010, the entire contents of each of which are incorporated by reference herein.

GOVERNMENT SUPPORT

This invention was made with government support under grant number GM062134 awarded by the National Institutes of Health. The government has certain rights in the invention.

FIELD OF THE INVENTION

This invention relates to activation of the complement cascade in the body. In particular, this invention provides peptides and peptidomimetics capable of binding the C3 protein and inhibiting complement activation.

BACKGROUND OF THE INVENTION

Various publications, including patents, published applications, technical articles and scholarly articles are cited throughout the specification. Each of these cited publications is incorporated by reference herein, in its entirety.

The human complement system is a powerful player in the defense against pathogenic organisms and the mediation of immune responses. Complement can be activated through three different pathways: the classical, lectin, and alternative pathways. The major activation event that is shared by all three pathways is the proteolytic cleavage of the central protein of the complement system, C3, into its activation products C3a and C3b by C3 convertases. Generation of these fragments leads to the opsonization of pathogenic cells by C3b and iC3b, a process that renders them susceptible to phagocytosis or clearance, and to the activation of immune cells through an interaction with complement receptors (Markiewski & Lambris, 2007, *Am J Pathol* 171: 715-727). Deposition of C3b on target cells also induces the formation of new convertase complexes and thereby initiates a self-amplification loop.

An ensemble of plasma and cell surface-bound proteins carefully regulates complement activation to prevent host cells from self-attack by the complement cascade. However, excessive activation or inappropriate regulation of complement can lead to a number of pathologic conditions, ranging from autoimmune to inflammatory diseases (Holers, 2003, *Clin Immunol* 107: 140-51; Markiewski & Lambris, 2007, supra; Ricklin & Lambris, 2007, *Nat Biotechnol* 25: 1265-75; Sahu et al., 2000, *J Immunol* 165: 2491-9). The development of therapeutic complement inhibitors is therefore highly desirable. In this context, C3 and C3b have emerged as promising targets because their central role in the cascade allows for the simultaneous inhibition of the initiation, amplification, and downstream activation of complement (Ricklin & Lambris, 2007, supra).

Compstatin was the first non-host-derived complement inhibitor that was shown to be capable of blocking all three activation pathways (Sahu et al., 1996, *J Immunol* 157: 884-91; U.S. Pat. No. 6,319,897). This cyclic tridecapeptide binds to both C3 and C3b and prevents the cleavage of native C3 by the C3 convertases. Its high inhibitory efficacy was confirmed by a series of studies using experimental models that pointed to its potential as a therapeutic agent (Fiane et al., 1999a, *Xenotransplantation* 6: 52-65; Fiane et al., 1999b, *Transplant Proc* 31:934-935; Nilsson et al., 1998 *Blood* 92: 1661-1667; Ricklin & Lambris, 2008, *Adv Exp Med Biol* 632: 273-292; Schmidt et al., 2003, *J Biomed Mater Res A* 66: 491-499; Soulika et al., 2000, *Clin Immunol* 96: 212-221). Progressive optimization of compstatin has yielded analogs with improved activity (Ricklin & Lambris, 2008, supra; WO2004/026328; WO2007/062249). One of these analogs is currently being tested in clinical trials for the treatment of age-related macular degeneration (AMD), the leading cause of blindness in elderly patients in industrialized nations (Coleman et al., 2008, *Lancet* 372: 1835-1845; Ricklin & Lambris, 2008, supra). In view of its therapeutic potential in AMD and other diseases, further optimization of compstatin to achieve an even greater efficacy is of considerable importance.

Earlier structure-activity studies have identified the cyclic nature of the compstatin peptide and the presence of both a β-turn and hydrophobic cluster as key features of the molecule (Morikis et al., 1998, *Protein Sci* 7: 619-627; W099/13899; Morikis et al., 2002, *J Biol Chem* 277:14942-14953; Ricklin & Lambris, 2008, supra). Hydrophobic residues at positions 4 and 7 were found to be of particular importance, and their modification with unnatural amino acids generated an analog with 264-fold improved activity over the original compstatin peptide (Katragadda et al., 2006, *J Med Chem* 49: 4616-4622; WO2007/062249).

While previous optimization steps have been based on combinatorial screening studies, solution structures, and computational models (Chiu et al., 2008, *Chem Biol Drug Des* 72: 249-256; Mulakala et al., 2007, *Bioorg Med Chem* 15: 1638-1644; Ricklin & Lambris, 2008, supra), the recent publication of a co-crystal structure of compstatin complexed with the complement fragment C3c (Janssen et al., 2007, *J Biol Chem* 282: 29241-29247; WO2008/153963) represents an important milestone for initiating rational optimization. The crystal structure revealed a shallow binding site at the interface of macroglobulin (MG) domains 4 and 5 of C3c and showed that 9 of the 13 amino acids were directly involved in the binding, either through hydrogen bonds or hydrophobic effects. As compared to the structure of the compstatin peptide in solution (Morikis et al., 1998, supra), the bound form of compstatin experienced a conformational change, with a shift in the location of the β-turn from residues 5-8 to 8-11 (Janssen et al., 2007, supra; WO2008/153963).

In view of the foregoing, it is clear that the development of modified compstatin peptides or mimetics with even greater activity would constitute a significant advance in the art.

SUMMARY OF THE INVENTION

The present invention provides analogs and mimetics of the complement-inhibiting peptide, compstatin, ICVVQD-WGHHRCT (cyclic C2-C12); SEQ ID NO:1), which have improved complement-inhibiting activity as compared to compstatin.

One aspect of the invention features a compound comprising a modified compstatin peptide (ICVVQDWGHHRCT (cyclic C2-C12); SEQ ID NO:1) or analog thereof, in which the Gly at position 8 is modified to constrain the backbone conformation of the peptide at that location. In one embodiment, the backbone is constrained by replacing the Gly with N-methyl Gly. The peptide may be further modified by one or more of: replacement of His at position 9 with Ala; replacement of Val at position 4 with Trp or an analog of Trp; replacement of Trp at position 7 with an analog of Trp; acetylation of the N-terminal residue; and replacement of Thr at position 13 with Ile, Leu, Nle, N-methyl Thr or N-methyl Ile. In particular embodiments, the analog of Trp at position 4 is 1-methyl Trp or 1-formyl Trp and the analog of Trp at position 7, if present, is a halogenated Trp.

Certain embodiments feature a compstatin analog comprising a peptide having a sequence of SEQ ID NO:2, which is:

Xaa1-Cys-Val-Xaa2-Gln-Asp-Xaa3-Gly-Xaa4-His-Arg-Cys-Xaa5 (cyclic C2-C12) in which Gly at position 8 is modified to constrain the backbone conformation of the peptide at that location, and wherein:

Xaa1 is Ile, Val, Leu, Ac-Ile, Ac-Val, Ac-Leu or a dipeptide comprising Gly-Ile;

Xaa2 is Trp or an analog of Trp, wherein the analog of Trp has increased hydrophobic character as compared with Trp;

Xaa3 is Trp, or an analog of Trp comprising a chemical modification to its indole ring wherein the chemical modification increases the hydrogen bond potential of the indole ring;

Xaa4 is His, Ala, Phe or Trp; and

Xaa5 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —NH$_2$.

In certain embodiments, Xaa2 participates in a nonpolar interaction with C3. In other embodiments, Xaa3 participates in a hydrogen bond with C3. In various embodiments, the analog of Trp of Xaa2 is a halogenated tryptophan, such as 5-fluoro-1-tryptophan or 6-fluoro-1-tryptophan. In other embodiments, the Trp analog at Xaa2 comprises a lower alkoxy or lower alkyl substituent at the 5 position, e.g., 5-methoxytryptophan or 5-methyltryptophan. In other embodiments, the Trp analog at Xaa 2 comprises a lower alkyl or a lower alkenoyl substituent at the 1 position, with exemplary embodiments comprising 1-methyltryptophan or 1-formyltryptophan. In other embodiments, the analog of Trp of Xaa3 is a halogenated tryptophan such as 5-fluoro-1-tryptophan or 6-fluoro-1-tryptophan. In particular embodiments, Xaa2 is 1-methyltryptophan or 1-formyltryptophan and Xaa3 optionally comprises 5-fluoro-1-tryptophan.

In certain embodiments, the Gly at position 8 is N-methylated, and Xaa1 is Ac-Ile, Xaa2 is 1-methyl-Trp or 1-formyl-Trp, Xaa3 is Trp, Xaa4 is Ala, and Xaa5 is Thr, Ile, Leu, Nle, N-methyl Thr or N-methyl Ile. In particular, Xaa5 may be Ile, N-methyl Thr or N-methyl Ile. In particular, the compstatin analog comprises any one of SEQ ID NOS: 5, 7, 8, 9, 10 or 11.

In some embodiments, the compound comprises a peptide produced by expression of a polynucleotide encoding the peptide. In other embodiments, the compound is produced at least in part by peptide synthesis. A combination of synthetic methods can also be used.

Another aspect of the invention features a compound of any of the preceding claims, further comprising an additional component that extends the in vivo retention of the compound. The additional component is polyethylene glycol (PEG) in one embodiment. The additional component is an albumin binding small molecule in another embodiment. In another embodiment, the additional component is an albumin binding peptide. The albumin binding peptide may comprise the sequence RLIEDICLPRWGCLWEDD (SEQ ID NO: 14). Particular embodiments comprise any one of SEQ ID NOS: 5, 7, 8, 9, 10 or 11 linked to the albumin binding peptide. Optionally, the compound and the albumin binding peptide are separated by a spacer. The spacer can be a polyethylene glycol (PEG) molecule, such as mini-PEG or mini-PEG 3.

Another aspect of the invention features compound that inhibits complement activation, comprising a non-peptide or partial peptide mimetic of any one of SEQ ID NOS: 5, 7, 8, 9, 10 or 11, wherein the compound binds C3 and inhibits complement activation with at least 500-fold greater activity than does a peptide comprising SEQ ID NO:1 under equivalent assay conditions.

The compstatin analogs, conjugates and mimetics of the invention are of practical utility for any purpose for which compstatin itself is utilized, as known in the art and described in greater detail herein. Certain of these uses involve the formulation of the compounds into pharmaceutical compositions for administration to a patient. Such formulations may comprise pharmaceutically acceptable salts of the compounds, as well as one or more pharmaceutically acceptable diluents, carriers excipients, and the like, as would be within the purview of the skilled artisan.

Various features and advantages of the present invention will be understood by reference to the detailed description, drawings and examples that follow.

DETAILED DESCRIPTION OF ILLUSTRATIVE EMBODIMENTS

Definitions:

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The term "about" as used herein when referring to a measurable value such as an amount, a temporal duration, and the like, is meant to encompass variations of ±20% or ±10%, in some embodiments ±5%, in some embodiments ±1%, and in some embodiments ±0.1% from the specified value, as such variations are appropriate to make and used the disclosed compounds and compositions.

The term "compstatin" as used herein refers to a peptide comprising SEQ ID NO:1, ICVVQDWGHHRCT (cyclic C2-C12). The term "compstatin analog" refers to a modified compstatin comprising substitutions of natural and unnatural amino acids, or amino acid analogs, as well as modifications within or between various amino acids, as described in greater detail herein, and as known in the art. When referring to the location particular amino acids or analogs within compstatin or compstatin analogs, those locations are sometimes referred to as "positions" within the peptide, with the positions numbered from 1 (Ile in compstatin) to 13 (Thr in compstatin). For example, the Gly residue occupies "position 8."

The terms "pharmaceutically active" and "biologically active" refer to the ability of the compounds of the invention to bind C3 or fragments thereof and inhibit complement activation. This biological activity may be measured by one or more of several art-recognized assays, as described in greater detail herein.

As used herein, "alkyl" refers to an optionally substituted saturated straight, branched, or cyclic hydrocarbon having from about 1 to about 10 carbon atoms (and all combinations and subcombinations of ranges and specific numbers of carbon atoms therein), with from about 1 to about 7 carbon atoms being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl. The term "lower alkyl" refers to an optionally substituted saturated straight, branched, or cyclic hydrocarbon having from about 1 to about 5 carbon atoms (and all combinations and subcombinations of ranges and specific numbers of carbon atoms therein). Lower alkyl groups include, but are not limited to, methyl, ethyl, n-propyl, isopropyl, n-butyl, isobutyl, t-butyl, n-pentyl, cyclopentyl, isopentyl and neopentyl.

As used herein, "halo" refers to F, Cl, Br or I.

As used herein, "alkanoyl", which may be used interchangeably with "acyl", refers to an optionally substituted a straight or branched aliphatic acylic residue having from about 1 to about 10 carbon atoms (and all combinations and subcombinations of ranges and specific numbers of carbon atoms therein), with from about 1 to about 7 carbon atoms being preferred. Alkanoyl groups include, but are not limited to, formyl, acetyl, propionyl, butyryl, isobutyryl pentanoyl, isopentanoyl, 2-methyl-butyryl, 2,2-dimethylpropionyl, hexanoyl, heptanoyl, octanoyl, and the like. The term "lower alkanoyl" refers to an optionally substituted straight or branched aliphatic acylic residue having from about 1 to about 5 carbon atoms (and all combinations and subcombinations of ranges and specific numbers of carbon atoms therein. Lower alkanoyl groups include, but are not limited to, formyl, acetyl, n-propionyl, iso-propionyl, butyryl, iso-butyryl, pentanoyl, iso-pentanoyl, and the like.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and have from about 6 to about 20 carbon atoms (and all combinations and subcombinations of ranges and specific numbers of carbon atoms therein), with from about 6 to about 12 carbon atoms being preferred. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy, among others.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen at selected locations on a molecule. Exemplary substituents include, for example, halo, alkyl, cycloalkyl, aralkyl, aryl, sulfhydryl, hydroxyl (—OH), alkoxyl, cyano (—CN), carboxyl (—COOH), acyl (alkanoyl: —C(=O)R); —C(=O)O-alkyl, aminocarbonyl (—C(=O)NH$_2$), —N-substituted aminocarbonyl (—C (=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term D-amino acid" refers to dextrorotatory alpha-amino acids. Unless specified otherwise, all amino acids referred to herein are L-amino acids.

"Hydrophobic" or "nonpolar" are used synonymously herein, and refer to any inter- or intra-molecular interaction not characterized by a dipole.

"PEGylation" refers to the reaction in which at least one polyethylene glycol (PEG) moiety, regardless of size, is chemically attached to a protein or peptide to form a PEG-peptide conjugate. "PEGylated means that at least one PEG moiety, regardless of size, is chemically attached to a peptide or protein. The term PEG is generally accompanied by a numeric suffix that indicates the approximate average molecular weight of the PEG polymers; for example, PEG-8,000 refers to polyethylene glycol having an average molecular weight of about 8,000.

As used herein, "pharmaceutically-acceptable salts" refers to derivatives of the disclosed compounds wherein the parent compound is modified by making acid or base salts thereof. Examples of pharmaceutically-acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

Description:

In accordance with the present invention, information about the biological and physico-chemical characteristics of compstatin binding to C3 have been employed to design modified compstatin peptides with significantly improved activity compared to the parent compstatin peptide. In some embodiments, the analogs have at least 300-fold greater activity than does compstatin. In other embodiments, the analogs have 350-, 400-, 450-, 500-, 550-, 600-fold or greater activity than does compstatin, as compared utilizing the assays described in the examples.

Compstatin analogs synthesized in accordance with previous approaches have been shown to possess improved activity as compared with the parent peptide, i.e., up to about 99-fold (Mallik, B. et al, 2005, supra; WO2004/026328), and up to about 264-fold (Katragadda et al., 2006, supra; WO2007/062249). The analogs produced in accordance with the present invention demonstrate improved activity via modification at a position of compstatin heretofore not utilized, and can impart improved activity to compstatin or any currently described analog. The analogs of the present invention thus possess even greater activity than either the parent peptide or analogs thereof produced to date, as demonstrated by in vitro assays as shown in the figures and in the Examples herein.

The table below shows amino acid sequence and complement inhibitory activities of selected exemplary analogs with significantly improved activity over compstatin (Ic[CVVQD-WGHHRC]T; SEQ ID NO:1). The selected analogs are referred to by specific modifications of designated positions (1-13) as compared to a potent compstatin analog (Ac-Ic[CV($^{1-Me}$W)QDWGAHRC]T-NH$_2$, SEQ ID NO:4, also referred to as peptide 14 in Example 1) which was described in WO2007/062249. The peptides of SEQ ID NOS: 5 and 7-11 (also referred to as peptides 15 and 17-21 in Example 1) are representative of modifications made in accordance with the present invention, resulting in significantly more potent compstatin analogs.

Exemplary compstatin analogs, IC$_{50}$, and fold change in activity relative to SEQ ID NO:4 (Ac-Ic[CV($^{1-Me}$W)QDW-GAHRC]T-NH$_2$), IC$_{50}$ of 206 nM):

8, 9, 10 and 11) as discussed in Example 1. Again, without intending to be limited or bound by theory, replacement of Thr with hydrophobic Ile was found to be beneficial. The similar effects observed for the two isomers of Ile (i.e., Leu and Nle) suggest that physicochemical and steric properties, rather than specific contacts, may be responsible for this improvement. However, a more distinct improvement in affinity and activity was observed upon backbone N-methylation of both Thr$^{13}$ and Ile$^{13}$. While the observed improvements may have resulted from increased backbone restraints, and hence lower conformational entropic penalties upon binding, it is also the case that the nature of the residue at position 13 can further influence the formation and stabilization of active conformations, either sterically or via formation of intramolecular hydrophobic contacts.

The above-described modifications at position 8 and position 13 can be combined with other modifications of compstatin previously shown to improve activity, to produce peptides with significantly improved complement inhibiting activity. For example, acetylation of the N-terminus typically

| SEQ ID NO: | Pept. No. | Xaa$^8$ | Xaa$^{13}$ | Sequence | IC$_{50}$ (nM) | Fold change |
|---|---|---|---|---|---|---|
| 5 | 15 | Sar* | Thr | Ac-Ic[CV($^{1-Me}$W)QDW($^{N-Me}$G)AHRC]T-NH$_2$ | 159 | 1.30 |
| 7 | 17 | Sar | Ile | Ac-Ic[CV($^{1-Me}$W)QDW($^{N-Me}$G)AHRC]I-NH$_2$ | 92 | 2.24 |
| 8 | 18 | Sar | Leu | Ac-Ic[CV($^{1-Me}$W)QDW($^{N-Me}$G)AHRC]L-NH$_2$ | 108 | 1.91 |
| 9 | 19 | Sar | Nle | Ac-Ic[CV($^{1-Me}$W)QDW($^{N-Me}$G)AHRC](Nle)-NH$_2$ | 109 | 1.90 |
| 10 | 20 | Sar | $^{(NMe)}$Thr | Ac-Ic[CV($^{1-Me}$W)QDW($^{N-Me}$G)AHRC]($^{N-Me}$T)-NH$_2$ | 86 | 2.40 |
| 11 | 21 | Sar | $^{(NMe)}$Ile | Ac-Ic[CV($^{1-Me}$W)QDW($^{N-Me}$G)AHRC]($^{N-Me}$I)-NH$_2$ | 62 | 3.32 |

*Sar = N-Me Gly

One modification in accordance with the present invention comprises constraint of the peptide backbone at position 8 of the peptide. In a particular embodiment, the backbone is constrained by replacing glycine at position 8 (Gly$^8$) with N-methyl glycine. Reference is made to exemplary peptides 8 and 15 as discussed in Example 1.

Without intending to be bound or limited by theory, it is noted that N-methylation can affect a peptide in several ways. First, the potential hydrogen bond donor is replaced with a methyl group, which cannot form a hydrogen bond. Second, the N-methyl group is weakly electron-donating which means it can slightly increase the basicity of the neighboring carbonyl group. Third, the size of the N-methyl group could cause steric constraint. Finally, the N-methylation can change the trans/cis population of the amide bond, thus changing local peptide conformation in a manner similar to a proline.

The activity increase of [Trp(Me)$^4$Gly(N-Me)$^8$Ala$^9$]-Ac-compstatin (SEQ ID NO:5; peptide 15) is a noteworthy improvement as compared to the previously most active analog, [Trp(Me)$^4$Gly$^8$Ala$^9$]-Ac-compstatin (SEQ ID NO:4; peptide 14). N-methylation of Gly$^8$ likely improves target recognition and complex stability by reinforced bound-like β-turn, increased local backbone constraints and improved hydrophobic interactions involving the side chain of Trp$^7$.

In particular embodiments, the modification at position 8 is supplemented with an additional modification comprising replacing Thr at position 13 with Ile, Leu, Nle (norleucine), N-methyl Thr or N-methyl Ile. Reference is made to exemplary peptides 16, 17, 18, 19, 20 and 21 (SEQ ID NOS: 6, 7, increases the complement-inhibiting activity of compstatin and its analogs. Accordingly, addition of an acyl group at the amino terminus of the peptide, including but not limited to N-acetylation, is one preferred embodiment of the invention, of particular utility when the peptides are prepared synthetically. However, it is sometimes of advantage to prepare the peptides by expression of a peptide-encoding nucleic acid molecule in a prokaryotic or eukaryotic expression system, or by in vitro transcription and translation. For these embodiments, the naturally-occurring N-terminus may be utilized.

As another example, it is known that substitution of Ala for His at position 9 improves activity of compstatin and is a preferred modification of the peptides of the present invention as well. It has also been determined that substitution of Tyr for Val at position 4 can result in a modest improvement in activity (Klepeis et al., 2003, *J Am Chem Soc* 125: 8422-8423).

It was disclosed in WO2004/026328 and WO2007/0622249 that Trp and certain Trp analogs at position 4, as well as certain Trp analogs at position 7, especially combined with Ala at position 9, yields many-fold greater activity than that of compstatin. These modifications are used to advantage in the present invention as well.

In particular, peptides comprising 5-fluoro-l-tryptophan or either 5-methoxy-, 5-methyl- or 1-methyl-tryptophan, or 1-formyl-tryptophan at position 4 have been shown to possess 31-264-fold greater activity than does compstatin. Particularly preferred are 1-methyl and 1-formyl tryptophan. It is believed that an indole 'N'-mediated hydrogen bond is not necessary at position 4 for the binding and activity of compstatin. The absence of this hydrogen bond or reduction of the polar character by replacing hydrogen with lower alkyl, alkanoyl or indole nitrogen at position 4 enhances the binding and activity of compstatin. Without intending to be limited to any particular theory or mechanism of action, it is believed that a hydrophobic interaction or effect at position 4 strengthens the interaction of compstatin with C3. Accordingly, modifications of Trp at position 4 (e.g., altering the structure of the side chain according to methods well known in the art), or substitutions at position 4 or position 7 of Trp analogs that maintain or enhance the aforementioned hydrophobic interaction are contemplated in the present invention as an advantageous modification in combination with the modifications at positions 8 and 13 as described above. Such analogs are well known in the art and include, but are not limited to the analogs exemplified herein, as well as unsubstituted or alternatively substituted derivatives thereof. Examples of suitable analogs may be found by reference to the following publications, and many others: Beene, et al., 2002, *Biochemistry* 41: 10262-10269 (describing, inter alia, singly- and multiply-halogenated Trp analogs); Babitzky & Yanofsky, 1995, *J. Biol. Chem.* 270: 12452-12456 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Trp analogs may be introduced into the compstatin peptide by in vitro or in vivo expression, or by peptide synthesis, as known in the art.

In certain embodiments, Trp at position 4 of compstatin is replaced with an analog comprising a 1-alkyl substituent, more particularly a lower alkyl (e.g., $C_1$-$C_5$) substituent as defined above. These include, but are not limited to, N($\alpha$) methyl tryptophan, N($\alpha$) formyl tryptophan and 5-methyl-tryptophan. In other embodiments, Trp at position 4 of compstatin is replaced with an analog comprising a 1-alkanoyl substituent, more particularly a lower alkanoyl (e.g., $C_1$-$C_5$) substituent as defined above. In addition to exemplified analogs, these include but are not limited to 1-acetyl-L-tryptophan and L-β-homotryptophan.

It was disclosed in WO2007/0622249 that incorporation of 5-fluoro-l-tryptophan at position 7 in compstatin increased enthalpy of the interaction between compstatin and C3, relative to wildtype compstatin, whereas incorporation of 5-fluoro-tryptophan at position 4 in compstatin decreased the enthalpy of this interaction. Accordingly, modifications of Tip at position 7, as described in WO2007/0622249, are contemplated as useful modifications in combination with the modifications to positions 8 and 13 as described above.

The modified compstatin peptides of the present invention may be prepared by various synthetic methods of peptide synthesis via condensation of one or more amino acid residues, in accordance with conventional peptide synthesis methods. For example, peptides are synthesized according to standard solid-phase methodologies, such as may be performed on an Applied Biosystems Model 431A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. During the course of peptide synthesis, branched chain amino and carboxyl groups may be protected/deprotected as needed, using commonly-known protecting groups. An example of a suitable peptide synthetic method is set forth in Example 1. Modification utilizing alternative protecting groups for peptides and peptide derivatives will be apparent to those of skill in the art.

Alternatively, certain peptides of the invention may be produced by expression in a suitable prokaryotic or eukaryotic system. For example, a DNA construct may be inserted into a plasmid vector adapted for expression in a bacterial cell (such as *E. coli*) or a yeast cell (such as *Saccharomyces cerevisiae*), or into a baculovirus vector for expression in an insect cell or a viral vector for expression in a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The peptides can also be produced by expression of a nucleic acid molecule in vitro or in vivo. A DNA construct encoding a concatemer of the peptides, the upper limit of the concatemer being dependent on the expression system utilized, may be introduced into an in vivo expression system. After the concatemer is produced, cleavage between the C-terminal Asn and the following N-terminal G is accomplished by exposure of the polypeptide to hydrazine.

The peptides produced by gene expression in a recombinant procaryotic or eucaryotic system may be purified according to methods known in the art. A combination of gene expression and synthetic methods may also be utilized to produce compstatin analogs. For example, an analog can be produced by gene expression and thereafter subjected to one or more post-translational synthetic processes, e.g., to modify the N- or C-terminus or to cyclize the molecule.

Advantageously, peptides that incorporate unnatural amino acids, e.g., methylated amino acids, may be produced by in vivo expression in a suitable prokaryotic or eukaryotic system. For example, methods such as those described by Katragadda & Lambris (2006, *Protein Expression and Purification* 47: 289-295) to introduce unnatural Trp analogs into compstatin via expression in *E. coli* auxotrophs may be utilized to introduce N-methylated or other unnatural amino acids at selected positions of compstatin.

The structure of compstatin is known in the art, and the structures of the foregoing analogs are determined by similar means. Once a particular desired conformation of a short peptide has been ascertained, methods for designing a peptide or peptidomimetic to fit that conformation are well known in the art. Of particular relevance to the present invention, the design of peptide analogs may be further refined by considering the contribution of various side chains of amino acid residues, as discussed above (i.e., for the effect of functional groups or for steric considerations).

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of the peptides of the invention, which possess the same backbone conformational features and/or other functionalities, so as to be sufficiently similar to the exemplified peptides to inhibit complement activation.

The use of peptidomimetics for the development of high-affinity peptide analogs is well known in the art (see, e.g., Vagner et al., 2008, *Curr. Opin. Chem. Biol.* 12: 292-296; Robinson et al., 2008, *Drug Disc. Today* 13: 944-951) Assuming rotational constraints similar to those of amino acid residues within a peptide, analogs comprising non-amino acid moieties may be analyzed, and their conformational motifs verified, by any variety of computational techniques that are well known in the art.

The modified compstatin peptides of the present invention can be modified by the addition of polyethylene glycol (PEG) components to the peptide. As is well known in the art, PEGylation can increase the half-life of therapeutic peptides and proteins in vivo. In one embodiment, the PEG has an average molecular weight of about 1,000 to about 50,000. In another embodiment, the PEG has an average molecular weight of about 1,000 to about 20,000. In another embodiment, the PEG has an average molecular weight of about 1,000 to about 10,000. In an exemplary embodiment, the PEG has an average molecular weight of about 5,000. The polyethylene glycol may be a branched or straight chain, and preferably is a straight chain.

The compstatin analogs of the present invention can be covalently bonded to PEG via a linking group. Such methods are well known in the art. (Reviewed in Kozlowski A. et al. 2001, *BioDrugs* 15: 419-29; see also, Harris J M and Zalipsky S, eds. Poly(ethylene glycol), Chemistry and Biological Applications, ACS Symposium Series 680 (1997)). Non-limiting examples of acceptable linking groups include an ester group, an amide group, an imide group, a carbamate group, a carboxyl group, a hydroxyl group, a carbohydrate, a succinimide group (including without limitation, succinimidyl succinate (SS), succinimidyl propionate (SPA), succinimidyl carboxymethylate (SCM), succinimidyl succinamide (SSA) and N-hydroxy succinimide (NHS)), an epoxide group, an oxycarbonylimidazole group (including without limitation, carbonyldimidazole (CDI)), a nitro phenyl group (including without limitation, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. In certain embodiments, the linking group is a succinimide group. In one embodiment, the linking group is NHS.

The compstatin analogs of the present invention can alternatively be coupled directly to PEG (i.e., without a linking group) through an amino group, a sulfhydral group, a hydroxyl group or a carboxyl group. In one embodiment, PEG is coupled to a lysine residue added to the C-terminus of compstatin.

As an alternative to PEGylation, the in vivo clearance of peptides can also be reduced by linking the peptides to certain other molecules or peptides. For instance, certain albumin binding peptides display an unusually long half-life of 2.3 h when injected by intravenous bolus into rabbits (Dennis et al., 2002, *J Biol Chem.* 277: 35035-35043). A peptide of this type, fused to the anti-tissue factor Fab of D3H44 enabled the Fab to bind albumin while retaining the ability of the Fab to bind tissue factor (Nguyen et al., 2006, *Protein Eng Des Sel.* 19: 291-297.). This interaction with albumin resulted in significantly reduced in vivo clearance and extended half-life in mice and rabbits, when compared with the wild-type D3H44 Fab, comparable with those seen for PEGylated Fab molecules, immunoadhesins, and albumin fusions. WO2007/062249 describes a compstatin analog fused with an albumin-binding peptide (ABP) and reports that the fusion protein is active in inhibiting complement activation. However, the synthesis was lengthy and the yield of fusion product was lower than desired. Example 2 herein sets forth improved synthesis strategies utilizing an ABP as well as an albumin-binding small molecule (ABM), and optionally employing a spacer between the components. Those procedures resulted in the production of conjugates of ABP- and ABM-compstatin analogs capable of inhibiting complement activation and also exhibiting extended in vivo survival. Indeed, the ABP was able to improve the half-life of a compstatin analog by 21 fold without significantly compromising its inhibitory activity. Thus, such conjugates enable the systemic administration of the inhibitor without infusion.

The complement activation-inhibiting activity of compstatin analogs, peptidomimetics and conjugates may be tested by a variety of assays known in the art. In one embodiment, the assay described in Example 1 is utilized. A non-exhaustive list of other assays is set forth in U.S. Pat. No. 6,319,897, WO99/13899, WO2004/026328 and WO2007/062249, including, but not limited to, (1) peptide binding to C3 and C3 fragments; (2) various hemolytic assays; (3) measurement of C3 convertase-mediated cleavage of C3; and (4) measurement of Factor B cleavage by Factor D.

The peptides and peptidomimetics described herein are of practical utility for any purpose for which compstatin itself is utilized, as known in the art. Such uses include, but are not limited to: (1) inhibiting complement activation in the serum, tissues or organs of a patient (human or animal), which can facilitate treatment of certain diseases or conditions, including but not limited to, age-related macular degeneration, rheumatoid arthritis, spinal cord injury, Parkinson's disease, Alzheimer's disease, cancer, and respiratory disorders such as asthma, chronic obstructive pulmonary disease (COPD), allergic inflammation, emphysema, bronchitis, bronchiectasis, cyctic fibrosis, tuberculosis, pneumonia, respiratory distress syndrome (RDS-neonatal and adult), rhinitis and sinusitis; (2) inhibiting complement activation that occurs during cell or organ transplantation, or in the use of artificial organs or implants (e.g., by coating or otherwise treating the cells, organs, artificial organs or implants with a peptide of the invention); (3) inhibiting complement activation that occurs during extracorporeal shunting of physiological fluids (blood, urine) (e.g., by coating the tubing through which the fluids are shunted with a peptide of the invention); and (4) in screening of small molecule libraries to identify other inhibitors of compstatin activation (e.g., liquid- or solid-phase high-throughput assays designed to measure the ability of a test compound to compete with a compstatin analog for binding with C3 or a C3 fragment).

To implement one or more of the utilities mentioned above, another aspect of the invention features pharmaceutical compositions comprising the compstatin analogs or conjugates described and exemplified herein. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-does unit.

As used herein, the term "pharmaceutically-acceptable carrier" means a chemical composition with which a complement inhibitor may be combined and which, following the combination, can be used to administer the complement inhibitor to a mammal.

The following examples are provided to describe the invention in greater detail. They are intended to illustrate, not to limit, the invention.

Example 1

A mono-$N^\alpha$-methylation scan was performed on [Tyr$^4$Ala$^9$]-Ac-compstatin (Ac-Ic[CVYQDWGAHRC]T-NH$_2$; SEQ ID NO:3). Based on the assay results of these analogs, selective N-methylation and substitution at position 13 was performed on [Trp(Me)$^4$Ala$^9$]-Ac-compstatin (Ac-Ic[CV($^{1-Me}$W)QDWGAHRC]T-NH$_2$; SEQ ID NO:4). Selected analogs were further characterized using surface plasmon resonance (SPR) and isothermal titration calorimetry (ITC). Molecular dynamics (MD) simulations were also performed to investigate possible mechanisms for the observed increase in affinity.

Materials and Methods:

Abbreviations.

Ac, acetyl group; Acm, acetamidomethyl; Boc, tert-butoxycarbonyl; CHARMM, Chemistry at Harvard Macromolecular Mechanics; DCM, dichloromethane; DIC, 1,3-diisopropylcarbodiimide; DIPEA, N,N-diisopropylethylamine; DMF, N,N-dimethyl-formamide; ELISA, enzyme-linked immunosorbent assay; ESI, electrospray ionization; Fmoc, 9-fluorenylmethoxycarbonyl; HOAt, 1-hydroxy-7-aza-benzotriazole; ITC, isothermal titration calorimetry; MALDI, matrix-assisted laser desorption ionization; MBHA, 4-methylbenz-hydrylamine; MOE, molecular operating environment; NAMD, nanoscale molecular dynamics; Nle, L-norleucine; NMP, N-methylpyrrolidinone; RMSD, root mean square deviation; SPR, surface plasmon resonance; TIPS, triisopropylsilane; Trt, trityl.

Chemicals.

Low-loading Rink amide MBHA resin and the following Fmoc-amino acids were obtained from Novabiochem (San Diego, Calif.): Ile, Cys(Acm), Val, Tyr(tBu), Gln(Trt), Asp (OtBu), Trp(Boc), Gly, Sar, Ala, MeAla, His(Trt), Arg(Pmc), MeIle, Nle, Phe, and Thr(tBu). DIC and Fmoc-Trp(Me)-OH were purchased from AnaSpec (San Jose, Calif.). HOAt was purchased from Advanced ChemTech (Louisville, Ky.). NMP and DCM were obtained from Fisher Scientific (Pittsburgh, Pa.). All other chemical reagents for synthesis were purchased from Sigma-Aldrich (St. Louis, Mo.) and used without further purification.

Peptide Synthesis and Purification.

All peptides were synthesized manually by Fmoc solid-phase methodology using DIC and HOAt as coupling reagents. When N-methylated amino acids were not commercially available, $N^\alpha$-methylation was performed by using the optimized methodology reported by Biron et al. (2006, *J Peptide Sci* 12:213-219). The following procedures were used for the synthesis of the linear peptides: Rink amide MBHA resin (294 mg, 0.34 mmol/g) was placed into a 10 mL HSW polypropylene syringe with fits on the bottom (Torviq, Niles, Mich.) and swollen in DCM (5 mL) for 30 min. After removal of the Fmoc protecting group (25% piperidine in NMP, 5 mL, 5 and 10 min), the resin was washed four times with NMP (5 mL per wash) and DCM (5 mL per wash), and the individual amino acids were coupled to the resin. For each coupling, 3 equivalents (3 mmol) of the amino acid, HOAt, and DIC were used, with 10 min preactivation in NMP. All couplings were performed for 1 h and monitored by either the Kaiser test or the chloranil test. In case of a positive test result, the coupling was repeated until a negative test result was observed.

The N-terminal amino group was acetylated with 20 equivalents of acetic anhydride and 2 equivalents of DIPEA in 5 mL of DCM for 30 min. Linear peptides containing Cyc(Acm) residues were cyclized on resin using thallium acetate in DMF/anisole (19:1) at ambient temperature for 3 h. The resin was washed four times with DMF, DCM, and DCM/diethylether (1:1) (each 5 mL per wash), and dried under vacuum for 4 h. The peptides were cleaved from the resin with a mixture of 95% TFA, 2.5% water, and 2.5% TIPS for 3 h. After evaporation of the TFA under vacuum, the peptides were precipitated and washed three times with 30 mL of cold diethyl ether per wash. The liquid was separated from the solid by centrifugation and decanted. The crude peptides were dried in air and dissolved in acetonitrile and 0.1% TFA in water (1:3) before purification by preparative RP-HPLC (Vydac $C_{18}$ 218TP152022 column, Western Analytical Products, Murrieta, Calif.) and elution with a linear gradient of 15-50% acetonitrile in aqueous 0.1% TFA solution over 35 min at a flow rate of 15 mL/min. Fractions containing the desired products were collected, concentrated, and lyophilized. The purified peptides were isolated in 10-15% overall yields and were >95% pure as determined by analytical RP-HPLC (Phenomenex 00G-4041-E0 Luna 5µ $C_{18}$ 100A column, 250×4.60 mm; Phenomenex, Torrance, Calif.). The mass of each peptide was confirmed using ThermoQuest Finnigan LCQ Duo and Waters MALDI micro MX instruments.

Purification of C3.

C3 was purified from fresh human plasma obtained from the blood bank of the Hospital of the University of Pennsylvania. In brief, the plasma was fractionated with 15% (w/v) PEG 3350, and the pellet was resuspended in 20 mM phosphate buffer, pH 7.8, and then subjected to anion-exchange chromatography on a DEAE-HR 40 column (50×5 cm; Millipore Inc., Billerica, Mass.) with the same buffer. Proteins were eluted with 6 L of a linear gradient (15-70%) of 20 mM phosphate buffer, pH 7.8, containing 500 mM NaCl. C3 was further purified on a size-exclusion Superdex 200 26/60 column (Amersham Biosciences) and a Mono S column (Amersham Biosciences) to separate C3 from C3(H$_2$O).

Inhibition of Complement Activation.

The ability of the compstatin analogs to inhibit the activation of the classical pathway of complement was assessed by ELISA (Mallik et al., 2005, *J Med Chem* 48:274-86). In brief, complement was activated in human serum using an antigen-antibody complex in the presence or absence of compstatin analogs, and the deposition of C3 fragments on the plate surface was detected using an HRP-conjugated polyclonal anti-C3 antibody. The absorbance data obtained at 405 nm were translated into % inhibition, based on the absorbance corresponding to 100% complement activation. The percent inhibition was plotted against the peptide concentration, and the resulting data set was fitted to the logistic dose-response function using Origin 7.0 software. IC$_{50}$ values were obtained from the fitted parameters that produced the lowest $\chi^2$ value. Each analog was assayed at least three to seven times. Standard deviations were all within 30% of the mean value.

ITC Analysis.

All ITC experiments were performed with the Microcal VP-ITC calorimeter (Microcal Inc., Northampton, Mass.), using protein concentrations of 1.8-5 µM C3 in the cell and peptide concentrations of 40-100 µM of individual compstatin analogs in the syringe. All titrations were performed in PBS (10 mM phosphate buffer with 150 mM NaCl, pH 7.4) at 25° C. using multiple peptide injections of 2-7 µL each. The raw isotherms were corrected for the heats of dilution by subtracting the isotherms representing peptide injections into the buffer. The resulting isotherms were fitted to a single site of sites models using Origin 7.0 software, and the model that produced the lowest $\chi^2$ value was deemed to be appropriate for the respective data set. The Gibbs free energy was calculated as $\Delta G=\Delta H-T\Delta S$. Each experiment was repeated at least twice. Errors were within 20% of the mean values.

SPR Analysis.

The kinetics of the interaction between C3b and each compstatin analog was analyzed by SPR on a Biacore 3000 instrument (GE Healthcare Corp., Piscataway, N.J.) at 25° C. using PBS-T (10 mM sodium phosphate, 150 mM NaCl, 0.005% Tween-20, pH 7.4) as the running buffer, as described above. In brief, biotinylated C3b (30 µg/mL) was immobilized on a streptavidin-coated sensor chip, and a two-fold serial dilution series (1 µM-500 pM) of each analog was injected for 2 min at 30 µl/min, with a dissociation phase of 5-10 min. Peptide [Trp(Me)$^4$]-Ac-compstatin was included in each experimental series as an internal control and reference. Data analysis was performed using Scrubber (BioLogic Software, Campbell, Australia). The signals from an untreated flow cell and an ensemble of buffer blank injections were subtracted to correct for buffer effects and injection artifacts. Processed biosensor data were globally fitted to a 1:1 Langmuir binding model, and the equilibrium dissociation constant ($K_D$) was calculated from the equation $K_D=k_d/k_a$. Peptide solutions were injected in duplicate in every experiment, and each screening assay was performed at least twice. The error of $k_a$ and $k_d$ were within 10% of mean values.

Molecular Dynamics Simulation.

All MD simulations were performed with the program NAMD (Phillips, et al., 2005, *J. Comput. Chem.* 26:1781-1802) using the CHARMM27 force field. For the free compstatin analogs, the NMR structure (Morikis & Lambris, 2002, *Biochem. Soc. Trans.* 30: 1026-1036) (PDB code: 1A1P) was adopted to build starting structures. Point mutations were introduced with the program Molecular Operating Environment (MOE, Chemical Computing Group, 2005). The mutated residues of the compstatin analogs were minimized using CHARMM (Brooks et al., 1983, *J. Comput. Chem.* 4: 187-217) version c33b1, with the CHARMM27 (MacKerell et al., 1998, *J. Phys. Chem. B* 102: 3586-3616) parameter set, while harmonic constraints were placed on the backbone atoms. The residues of complement C3c that were missing from the crystal structure were added using homology modeling and also minimized using CHARMM.

The crystallographic water molecules in the PDB file were maintained, and the structures were solvated in cubic periodic boxes of TIP3P (Jorgensen et al., 1983, *J. Chem. Phys.* 79: 926-935) water molecules. The distances between the edges of the water simulation box and the closest atom of solutes were at least 10 Å. Sodium and chloride counterions were then added using the VMD program (Humphrey et al., 1996, *J. Mol. Graphics* 14: 33-38, 27-28) in order to maintain the electroneutrality of the systems.

The systems were first minimized in three consecutive steps, during which the protein was initially held fixed and the water molecules were allowed to move for 10,000 conjugate gradient steps; next, only the protein backbone was held fixed for 100,000 steps; finally, all atoms were allowed to move for an additional 10,000 steps. The particle mesh Ewald method (Darden et al., 1993, *J. Chem. Phys.* 98: 10089-10092) was used to treat long-range electrostatic interactions in periodic boundary conditions with a grid of approximately 1 point per Å. Nonbonded van der Waals interactions were smoothly switched over 3 Å between 9 and 12 Å. Bond lengths involving bonds to hydrogen atoms were constrained by using SHAKE (Ryckaert et al., 1977, *J. Comput. Phys.* 23: 327-341). The time step for all MD simulation was 2 fs. The Nose-Hoover Langevin piston (Feller et al., 1995, *J. Chem. Phys.* 103: 4613-4621; Martyna et al., 1994, *J. Chem. Phys.* 101: 4177-4189) was used for pressure control, with the piston period set to 200 fs and a piston decay of 100 fs. MD simulations at 100 ps were carried out at constant volume, during which the systems were heated to 310 K in increments of 30 K; a subsequent isothermal isobaric MD simulation was used for 20 ns and 5 ns to adjust the solvent density without any restraints on all the solute atoms for free compstatin analogs and complexes, respectively. Finally, lowest energy structures were obtained from MD-equilibrated trajectory files and subsequently used in structure and entropy contribution analysis.

Results:

Inhibition of Complement Activation.

A backbone N-methylation scan was performed on a [Tyr$^4$Ala$^9$]-Ac-compstatin template (peptide 1; SEQ ID NO:3) to generate analogs 2-13 (Table 1-1). Although peptide 1 was less potent than the current lead compound, [Trp(Me)$^4$Ala$^9$]-Ac-compstatin (peptide 14, SEQ ID NO:4), it was chosen for the initial scan because of its lower cost of synthesis. The ability of each peptide to inhibit the activation of complement was then evaluated by ELISA and compared to the activity of peptide 1 (Table 1-1). The most negative effect was observed for the N-methylation of Val$^3$, Tyr$^4$ and Ala$^9$, which rendered peptides 3, 4, and 9 completely inactive. In contrast, N-methylation of Gly$^8$ and Thr$^{13}$ produced peptides 8 and 13 with slightly increased potency (1.7- and 1.3-fold, respectively). N-methylation in all other positions resulted in detectable, yet significantly reduced inhibitory activity (Table 1-1).

TABLE 1-1

Inhibition of classical pathway activation of complement by N$^\alpha$-methylated analogs of [Tyr$^4$ Ala$^9$]-Ac-compstatin (peptide 1; SEQ ID NO: 3)

| Peptide | Sequence | IC$_{50}$ (CP, µM) | IC$_{50}$-fold change[a] |
|---|---|---|---|
| 1[b] | Ac-I[CVYQDWGAHRC]T-NH$_2$ (SID 3) | 2.4 | 1 |
| 2 | Ac-I[(NMe)CVYQDWGAHRC]T-NH2 | 7.5 | 0.3 |
| 3 | Ac-I[C(NMe)VYQDWGAHRC]T-NH2 | NA | NA |
| 4 | Ac-I[CV(NMe)YQDWGAHRC]T-NH2 | NA | NA |

TABLE 1-1-continued

Inhibition of classical pathway activation of complement by
N$^\alpha$-methylated analogs of [Tyr$^4$ Ala$^9$]-Ac-compstatin
(peptide 1; SEQ ID NO: 3)

| Peptide | Sequence | IC$_{50}$ (CP, µM) | IC$_{50}$-fold change$^a$ |
|---|---|---|---|
| 5 | Ac-I[CVY(NMe)QDWGAHRC]T-NH2 | 33 | 0.07 |
| 6 | Ac-I[CVYQ(NMe)DWGAHRC]T-NH2 | 44 | 0.06 |
| 7 | Ac-I[CVYQD(NMe)WGAHRC]T-NH2 | 25 | 0.1 |
| 8 | Ac-I[CVYQDW(NMe)GAHRC]T-NH2 | 1.43 | 1.7 |
| 9 | Ac-I[CVYQDWG(NMe)AHRC]T-NH2 | NA | NA |
| 10 | Ac-I[CVYQDWGA(NMe)HRC]T-NH2 | 94 | 0.03 |
| 11 | Ac-I[CVYQDWGAH(NMe)RC]T-NH2 | 32 | 0.08 |
| 12 | Ac-I[CVYQDWGAHR(NMe)C]T-NH2 | 154 | 0.02 |
| 13 | Ac-I[CVYQDWGAHRC](NMe)T-NH2 | 1.89 | 1.3 |

Note:
$^a$relative to peptide 1. NA: not active,
$^b$Data from Sahu et al., 1996, J. Immunol. 157: 884-891.

We then applied the findings from the N-methylation scan to the a current potent analog, Ac-I[CV($^{1-Me}$W)QDW-GAHRC]T-NH$_2$ (SEQ ID NO:4; also referred to herein as [Trp(Me)$^4$ Ala$^9$]-Ac-compstatin, peptide 14), and synthesized analogs with selective N-methylation and amino acid substitutions at positions 8 and 13 (peptides 15-23; Table 1-2). Since previous studies had indicated limitations for substituting the side chain at position 8 (Morikis et al., 1998, *Protein Sci.* 7: 619-627; Furlong et al., 2000, *Immunopharmacology* 48: 199-212), modifications were restricted to the absence (Gly$^8$) or presence of N-methylation (NMeGly$^8$, i.e. Sar$^8$). In contrast, previous work showed that the C-terminal position 13 allowed more flexibility for substitutions and had even suggested a preference for Ile over Thr (Morikis & Lambris, 2002, *Biochem. Soc. Trans.* 30: 1026-1036). We therefore further investigated the importance of position 13 and designed a series of Sar$^8$ analogs to include various N-methylated, hydrophobic, or aromatic residues in this position. Consistent with the results from the N-methylation scan, the introduction of a single N-methyl group at position 8 (Sar$^8$; peptide 15) increased the inhibitory potency by 1.3-fold (Table 1-3). In addition, replacement of Thr by Ile at position 13 led to a significant increase for both the Gly$^8$ and Sar$^8$ peptides. However, neither the substitution of Ile by Leu or Nle, nor the introduction of His or Phe produced any improvement over the Ile$^{13}$ analog. In contrast, N-methylation of both Thr$^{13}$ and Ile$^{13}$ resulted in a significant increase in inhibitory activity (IC$_{50}$=86 and 62 nM, respectively), generating the most potent compstatin analogs described thus far.

TABLE 1-2

Evaluation of inhibitory potency, kinetic, and thermodynamic parameters for a series of compstatin analogs (Ac-Ile-c[Cys-Val-Trp(1-Me)-Gln-Asp-Trp-Gly-Ala-His-Arg-Cys]-Thr-NH$_2$) (peptide 14, SEQ ID NO: 4) with modifications in position 8 and 13. (Numbers in parentheses next to peptide numbers are SEQ ID NOs).

| No. | Xaa$^8$ | Xaa$^{13}$ | IC$_{50}$ (nM) | k$_a$ (10$^6$/Ms) | k$_d$ (10$^{-3}$/s) | K$_{D\,SPR}$ (nM) | K$_{D\,ITC}$ (nM) | ΔH (kcal/mol) | −TΔS (kcal/mol) | ΔG (kcal/mol) |
|---|---|---|---|---|---|---|---|---|---|---|
| 14 (4) | Gly | Thr | 206 | 1.0 | 11.3 | 11.9 | 15.0 | −17.6 | 6.9 | −10.7 |
| 15 (5) | Sar | Thr | 159 | 1.3 | 7.2 | 5.5 | 8.5 | −11.7 | 0.6 | −11.1 |
| 16 (6) | Gly | Ile | 154 | 1.0 | 11.0 | 11.0 | 12.1 | −16.6 | 5.7 | −10.9 |
| 17 (7) | Sar | Ile | 92 | 1.5 | 6.6 | 4.4 | 6.3 | −14.1 | 2.9 | −11.2 |
| 18 (8) | Sar | Leu | 108 | 1.3 | 6.0 | 4.6 | N/D | N/D | N/D | N/D |
| 19 (9) | Sar | Nle | 109 | 1.5 | 6.6 | 4.4 | N/D | N/D | N/D | N/D |
| 20 (10) | Sar | (NMe)Thr | 86 | 1.3 | 5.1 | 3.9 | 7.2 | −17.5 | 6.4 | −11.1 |
| 21 (11) | Sar | (NMe)Ile | 62 | 1.5 | 3.5 | 2.3 | 4.5 | −17.1 | 5.7 | −11.4 |
| 22 (12) | Sar | His | 160 | N/D | N/D | N/D | N/D | N/D | N/D | N/D |
| 23 (13) | Sar | Phe | 257 | N/D | N/D | N/D | N/D | N/D | N/D | N/D |

Binding Kinetic Characterization.

Peptides 15-21 were further characterized by SPR in order to evaluate the effect of individual substitutions on the kinetic profile and binding affinity for C3b (Table 1-2). In general, the relative K$_D$ values showed good consistency with the ELISA results (R$^2$=0.79; Table 1-3). N-methylation of Gly$^8$ (peptides 14 to 15, 16 to 17) clearly improved the binding kinetics and affinity, with significant effects on both kinetic rate constants. In contrast, the Thr-to-Ile substitutions (peptides 14 to 16, 15 to 17) had only slight, yet still beneficial impact on the SPR profiles. Again, the combination of both substitutions (peptide 17) had a synergistic effect, with a 2.7-fold stronger affinity than peptide 14, as compared to the impact of the Sar$^8$ and Ile$^{13}$ modifications alone (2.2- and 1.1-fold, respectively). Substitutions at position 13 alone appeared to primarily influence the dissociation rate ($k_d$=3.4-7.2×10$^{-3}$ s$^{-1}$); the association rate remained essentially constant for all Sar$^8$ analogs ($k_a$=1.3-1.7×10$^6$ M$^{-1}$s$^{-1}$). In this series, N-methylation of Thr$^{13}$ (peptide 20) and Ile$^{13}$ (peptide 21) again had the strongest impact on the dissociation rate, rendering analog 21 the strongest binder, with a more than 5-fold increase in affinity over peptide 14. The evaluated isomers of Ile$^{13}$ (Leu, Nle; peptides 18 and 19) had a negligible influence on the kinetic profile and affinity, indicating a common binding mode for this scaffold.

Characterization of Binding Thermodynamics.

ITC experiments were performed for peptides 15-17 and 20-21 in order to correlate the observed effects on affinity and potency with their thermodynamic profiles (Table 1-2 and 1-3). Although the absolute $K_D$ values in ITC tended to be slightly higher than those from SPR, they were highly correlated with the ELISA and SPR results ($R^2$=0.89 and 0.96, respectively). The highly beneficial enthalpy value ($\Delta H$=−17.6 kcal/mol) of the previous lead compound (peptide 14) was not surpassed by any of the newly designed analogs. In contrast, the entire panel had significantly improved entropy values (−$T\Delta S$=0.6–5.7 kcal/mol) when compared to peptide 14 (−$T\Delta S$=6.9 kcal/mol).

TABLE 1-3

Relative improvement in the potency and binding parameters of newly designed compstatin analogs when compared to [Trp(Me)$^4$ Ala$^9$]-Ac-compstatin (peptide 14)

| No. | Xaa$^8$ | Xaa$^{13}$ | rP | r$k_a$ | r$k_d$ | r$K_{D\,SPR}$ | r$K_{D\,ITC}$ | $\Delta\Delta H$ (kcal/mol) | −$T\Delta\Delta S$ (kcal/mol) | $\Delta\Delta G$ (kcal/mol) |
|---|---|---|---|---|---|---|---|---|---|---|
| 14 | Gly | Thr | 1.0 | 1.0 | 1.0 | 1.0 | 1.0 | 0 | 0 | 0 |
| 15 | Sar | Thr | 1.3 | 1.3 | 1.6 | 2.2 | 1.8 | 5.9 | −6.3 | −0.4 |
| 16 | Gly | Ile | 1.3 | 1.0 | 1.0 | 1.1 | 1.2 | 1.0 | −1.3 | −0.2 |
| 17 | Sar | Ile | 2.2 | 1.5 | 1.7 | 2.7 | 2.4 | 3.5 | −4.1 | −0.5 |
| 18 | Sar | Leu | 1.9 | 1.3 | 1.9 | 2.6 | N/D | N/D | N/D | N/D |
| 19 | Sar | Me | 1.9 | 1.5 | 1.7 | 2.7 | N/D | N/D | N/D | N/D |
| 20 | Sar | (NMe)Thr | 2.4 | 1.3 | 2.2 | 3.1 | 2.4 | 0.1 | −0.5 | −0.4 |
| 21 | Sar | (NMe)Ile | 3.3 | 1.5 | 3.2 | 5.2 | 3.3 | 0.5 | −1.3 | −0.7 |
| 22 | Sar | His | 1.3 | N/D | N/D | N/D | N/D | N/D | N/D | N/D |
| 23 | Sar | Phe | 0.8 | N/D | N/D | N/D | N/D | N/D | N/D | N/D |

Peptide 15 (Sar$^8$Thr$^{13}$; −$T\Delta S$=0.6 kcal/mol) exhibited the lowest entropic penalty of all the reported compstatin analogs. However, the majority of this large entropic gain was offset by a loss of favorable enthalpy ($\Delta\Delta H$=5.9 kcal/mol). Similar trends were observed for the entire panel, indicating the influence of enthalpy-entropy compensation. Additional substitution of Ile$^{13}$ for Thr$^{13}$ as in peptide 17 recaptured some of the lost enthalpy ($\Delta H$=−14.1 kcal/mol), while yielding some of the entropy gain (−$T\Delta S$=2.9 kcal/mol) in peptide 15. N-methylation in position 13, as in peptides 20-21, brought their enthalpy values even closer to that of peptide 14. Overall, the increased binding affinity for these peptides appeared to be achieved mainly by a reduction in entropic penalty. Furthermore, the ITC data confirmed the SPR results indicating that it was the Sar$^{8'}$ and not the Ile$^{13}$ substitution that contributed most to the largely increased affinity of peptide 17.

MD Simulations.

The large impact of even small peptide modifications on the thermodynamic profiles of the analogs was further investigated using MD simulations based on the NMR structure of compstatin and the crystal structure of [Trp$^4$]-Ac-compstatin with C3c (Morikis et al., 1998, supra; Janssen et al., 2007, *J. Biol. Chem.* 282: 29241-29247). In the case of N-methylation at position 8 (peptide 17), we suspected that this modification affected the side chain of the critical residue Trp$^7$, which is directly connected to the methylated Gly$^8$ nitrogen and occupies a tight pocket. MD simulations were therefore performed to compare the distribution of water molecules in the Trp$^7$ binding pockets of peptides 14 and 17. We found that whereas four water molecules could be observed for peptide 14, none were found after repeating the simulation with peptide 17. This result indicates that N-methylation at position 8 allows the side chain of Trp$^7$ to better fit into the C3c binding pocket.

Previous comparisons between the solution-based and protein-bound structures have revealed significant conformational rearrangement, including a shift in the important β-turn (Janssen et al., 2007, supra). Since N-methylation has been reported to affect the local conformation of the peptide backbone, we performed MD simulations for peptide 14 and 17 in the absence and presence of C3c and then compared the resulting lowest energy conformers of the free and bound peptides (Chatterjee et al., 2008, *Acc. Chem. Res.* 41: 1331-1342). The results showed that the β-turn encompassing residues 5-8 opened, and a new turn was formed between residues 8 and 11 in the free structures of both peptides. Also, the β-turns overlaid well with those in the bound structures. However, an intramolecular hydrogen bond between Trp$^7$ and Arg$^{11}$ with a distance of 2.9 Å was formed only in the case of peptide 17, likely constraining the conformation of free 17 and making it more rigid.

Example 2

This example describes an improved synthesis, and plasma half-life determination, of a compstatin analog (peptide 17 described in Example 1: Ac-Ile-c[Cys-Val-Trp(Me)-Gln-Asp-Trp-Sar-Ala-His-Arg-Cys]-Ile-NH$_2$; SEQ ID NO:7) conjugated to an albumin-binding peptide (ABP) or an albumin-binding small molecule (ABM), shown below.

ABP: Ac-RLIEDICLPRWGCLWEDD-NH$_2$ (C—C disulfide bond) (SEQ ID NO:14)

ABM:

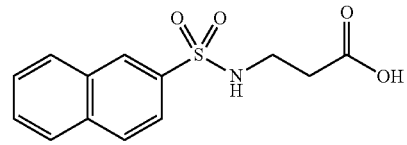

Two mini-PEG-3 molecules were used as a spacer and coupled to the C-terminal of peptide 17.

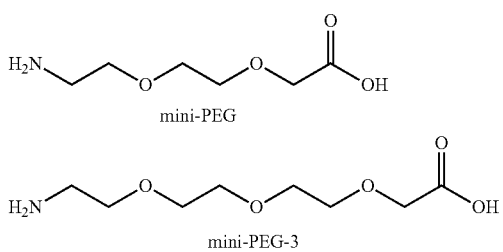

For comparison, the plasma half-life of the unconjugated peptide 17 was also determined.

Materials and Methods:

Abbreviations.

Ac, acetyl group; Acm, acetamidomethyl; Acm, acetamidomethyl; DCM, dichloromethane; DIC, 1,3-diisopropylcarbodiimide; DIPEA, N,N-diisopropylethylamine; DMF, N,N-dimethyl-formamide; ELISA, enzyme-linked immunosorbent assay; ESI, electrospray ionization; Fmoc, 9-fluorenylmethoxycarbonyl; HLB, hydrophilic-lipophilic balanced; HOAt, 1-hydroxy-7-aza-benzotriazole; HSW, Henke Sass Wolf; ITC, isothermal titration calorimetry; MALDI, matrix-assisted laser desorption ionization; MBHA, 4-methylbenz-hydrylamine; Mmt, Monomethoxytrityl; NanoESI, nanoelectrospray ionization; NMP, N-methylpyrrolidinone; PyBOP, benzotriazol-1-yl-oxytripyrrolidinophosphonium hexafluorophosphate; SPR, surface plasmon resonance; TBTA, Tris-(benzyltriazolylmethyl)amine; TEA, triethylamine; TFA, trifluoroacetic acid; TIPS, triisopropylsilane; Trt, trityl.

Materials.

DIC and Fmoc-Trp(Me)-OH were purchased from AnaSpec (San Jose, Calif.). Low-loading NovaSyn® TGR resin and other Fmoc-amino acids were obtained from Novabiochem (San Diego, Calif.). Mini-PEG and mini-PEG-3 were purchased from Peptide International (Louisville, Ky.). HOAt was purchased from Advanced ChemTech (Louisville, Ky.). ABM was obtained from Enamine Ltd. (Kiev, Ukraine). NMP and DCM were obtained from Fisher Scientific (Pittsburgh, Pa.). Water was purified using a Milli-Q water purification system (Millipore Corporate, Billerica, Mass.). All other chemical reagents for synthesis were purchased from Sigma-Aldrich (St. Louis, Mo.) and used without further purification.

Synthesis of Linear Peptides (Peptide 17-Mini-(PEG-3)$_2$-Lys(Mmt)-NH$_2$ and ABP).

All peptides were synthesized manually by Fmoc solid-phase methodology using DIC and HOAt as coupling reagents. In brief, resin (294 mg, 0.34 mmol/g) was placed into a 10 mL HSW polypropylene syringe with frits on the bottom (Torviq, Niles, Mich.) and swollen in DCM (5 mL) for 30 min. After removal of the Fmoc protecting group (25% piperidine in NMP, 5 mL, 5 and 10 min), the resin was washed four times with NMP (5 mL per wash) and DCM (5 mL per wash), and the individual amino acids were coupled to the resin. For each coupling, 3 equivalents (0.3 mmol) of the amino acid, HOAt, and DIC were used, with 10 min preactivation in NMP. All couplings were performed for 1 h and monitored to completion by either the Kaiser test or the chloranil test. If necessary, the N-terminal amino group was acetylated with 20 equivalents of acetic anhydride and 2 equivalents of DIPEA in 5 mL of DCM for 30 min.

Peptide Cyclization, Modification and Cleavage.

Linear peptides containing Cyc(Acm) residues were cyclized on-resin using 1.2 equivalent of thallium trifluoroacetate in DMF/anisole (19:1) at ambient temperature for 3 h. To synthesize azido-peptide 17, the side chain Mmt protecting group of the C-terminal Lys of the peptide 17 derivative was removed using 1% TFA in DCM with 5% TIPS. Then, 2-azidoacetic acid was coupled to the side chain using PyBOP/HOAt/DIPEA in NMP. Peptide 17-ABM was synthesized in similar way. To synthesize Alkyne-ABP, propiolic acid was coupled to the N-terminal of ABP using DIC/HOAt in NMP/DCM (1:1). Resin was thoroughly washed with DCM, DCM/diethylether (1:1), and dried under high vacuum for 4 h before the peptides were cleaved in a mixture of 95% TFA, 2.5% water, and 2.5% TIPS for 2 h. After evaporation of the TFA under vacuum, the peptides were precipitated and washed three times with 30 mL of cold diethyl ether per wash. The liquid was separated from the solid by centrifugation and decanted. The crude peptides were dried in air and dissolved in acetonitrile and 0.1% TFA in water (1:3) for HPLC purification.

Cupper(I) Mediated Azide-Alkyne Huisgen Cycloaddition for the Synthesis of Peptide 17-ABP.

50 mg (22 µmol) of each purified azide and alkyne peptide was dissolved in 5 mL of t-BuOH/H$_2$O (2:1). 10 equiv (220 µmol) of TEA was added to make the solution basic. Then 5% (1.1 µmol) of CuSO$_4$, 25% of sodium ascorbic acid, and 1% of TBTA was added to the mixture. The mixture was stirred overnight, monitored by HPLC-MS. It was then concentrated under vacuum and purified by reverse phase HPLC.

Peptide Purification.

The peptides were injected into a preparative RP-HPLC column (Xbridge™ BEH130 Prep C18 5 µm 19×150 mm, PN #186003945, Waters, Milford, Mass.) and eluted with a linear gradient of 15-50% acetonitrile in 0.1% TFA over 15 min at a flow rate of 20 mL/min. Fractions containing the desired products were collected baseD on mass, and lyophilized. The purified peptides were >95% pure as determined by analytical RP-HPLC (Xbridge™ BEH130 C18 5 µm, 4.6×150 mm, PN #186003580, Waters, Milford, Mass.). The mass of each peptide was confirmed using Waters MALDI micro MX instruments or SYNAPT HDMS.

Inhibition of Complement Activation.

The ability of the compstatin analogs to inhibit the activation of the classical pathway of complement was assessed by ELISA as described in Example 1. Each conjugate was assayed at least three times.

SPR Analysis.

The kinetics of the interaction between C3b and each compstatin analog was analyzed by SPR on a Biacore 3000 instrument (GE Healthcare Corp., Piscataway, N.J.) at 25° C. using PBS-T (10 mM sodium phosphate, 150 mM NaCl, 0.005% Tween-20, pH 7.4) as the running buffer, as described in Example 1. In brief, biotinylated C3b (30 µg/ml) was immobilized on a streptavidin-coated sensor chip, and a two-fold serial dilution series (1 µM-500 pM) of each analog was injected for 2 min at 30 µl/min, with a dissociation phase of 5-10 min. Peptide 17 (unconjugated) was included in each experimental series as an internal control and reference. Data analysis was performed using Scrubber (BioLogic Software, Campbell, Australia). The signals from an untreated flow cell and an ensemble of buffer blank injections were subtracted to correct for buffer effects and injection artifacts. Processed biosensor data were globally fitted to a 1:1 Langmuir binding model, and the equilibrium dissociation constant ($K_D$) was calculated from the equation $K_D=k_d/k_a$. Peptide solutions were injected in duplicate in every experiment, and each screening assay was performed at least twice.

Extraction of Compstatin Analogs from Plasma Samples by SPE.

A 96-well plate HLB Oasis 10 mg (Waters, Milford, Mass.) was employed for extraction. The SPE material was conditioned by addition of 500 μl of methanol followed by addition of 500 μL of milli-Q water. Sample was prepared by addition of the internal standard followed by 1:1 dilution with 4% $H_3PO_4$. After loading the sample, washing was carried out with 500 μL of 5% methanol in 0.1% formic acid. Sample was eluted with 150 μL of 65% methanol in 0.1% formic acid and collected in the collection plate. Solvent was evaporated to dryness in a speed-vac concentrator and reconstituted in 5% acetonitrile in 0.1% formic acid. Samples were kept at −20° C. until analysis.

Isolation of Peptide 17-ABP and Peptide 17-ABM from Plasma Samples by Digestion.

Baboon plasma samples, 40 μL, were mixed with internal standard and dissolved 1:1 with 40 mM ammonium carbonate buffer. Rapigest detergent was added to a final concentration of 0.1%. Disulfide bridges were reduced in 5 mM DTT for 30 min at 60° C. Alkylation of cysteines was done by addition of iodoacetamide to a final concentration of 15 mM and incubation for 30 min in dark. The sample was enzymatically digested by addition of 16 μL of a 1 μG/μL trypsin solution and incubation overnight at 37° C. After that, the sample pH was lowered with 5% TFA to induce detergent degradation. To avoid nonspecific adsorption of very hydrophobic peptides, acetonitrile was added to 20%. The samples were centrifuged at 6° C. and 14000 rpm for 30 min and the supernatant was diluted with 0.1% formic acid to reduce acetonitrile concentration to 10% prior to filtration with a 10 kDa cut-off microcon centrifugal filter (Millipore, Billerica, Mass.). The filter was washed with 50 μL of 10% ACN in 0.1% formic acid and the collected sample was evaporated to dryness and reconstituted with 10% ACN in 0.1% formic acid.

LC-MS/MS Analysis.

LC-MS/MS analysis was performed on a SYNAPT HDMS (Waters, Milford, Mass.) controlled by MassLynx 4.1 software (Waters) and equipped with a nanoESI source. Each sample was injected in triplicate. A nanoACQUITY UPLC (Waters) system was used for peptide separation by reversed-phase liquid chromatography. After injection, analytes were trapped for 3 min with 3% mobile phase A (0.1% formic acid in water) at 5 μl/min on a 5 μm Symmetry C18 column (180 μm×20 mm, Waters) and further separated on a 1.7 μm BEH130 C18 column (75 μm×150 mm, Waters). The analytical column temperature was held at 35° C. Peptides were separated at flow rate 0.3 μl/min. The gradient was linear 3-40% B (0.1% formic acid in acetonitrile), either 50 min long, or 60 min for the digested samples. The capillary voltage was 3.2 kV, the cone voltage was 35 V and the source temperature was 100° C. [Glu1]-fibrinogen peptide was used for lock-mass correction with a sampling rate of 30 s. Mass spectra were acquired in positive mode over an m/z range 400-2000 Da at scan rate 0.6 s. The time window used for the MS/MS function was ±3 min of the retention time of the selected peptide. The presence of the analyte was confirmed by MS/MS. Selectivity was studied by analysis of blank samples to determine the presence of any interference coeluting with the analyte.

In Vivo Retention.

Juvenile baboons (*P. Anubis*, Baboon Research Resources, University of Oklahoma) weighing 5-8 kg were used. Three baboons were used for the study; one for each compound. All animals received a bolus dose of peptides (10 mg) by injection through the peripheral vein. Blood samples for the LC-MS/MS assay were collected in 1-ml plastic tubers containing 50 μg lepirudin and centrifuged at 2000 g for 20 min at 4° C. for plasma separation. Plasma samples were stored at −70° C. Blood samples were collected at 20, 40, 60 90, 120 min after injection of peptide 17; and 1 min, 30 min then 1, 6, 24 and 48 hrs after injection of peptide 17-ABP and peptide 17-ABM.

Results:

Synthesis of Peptide 17-ABM.

Peptide 17-ABM was obtained after solid phase peptide synthesis and HPLC purification, as summarized in the reaction scheme below. The linear peptide was synthesized with a single coupling of each amino acid. Both thallium trifluoroacetate and iodine was evaluated for the disulfide bond formation. The former yielded cleaner reactions and was thereafter used for all cyclizations. The mass of peptide 17-ABM was confirmed by HPLC-MS and ESI-TOF ([MH]$^{2+}$ calc. 1211.06. found 1211.05).

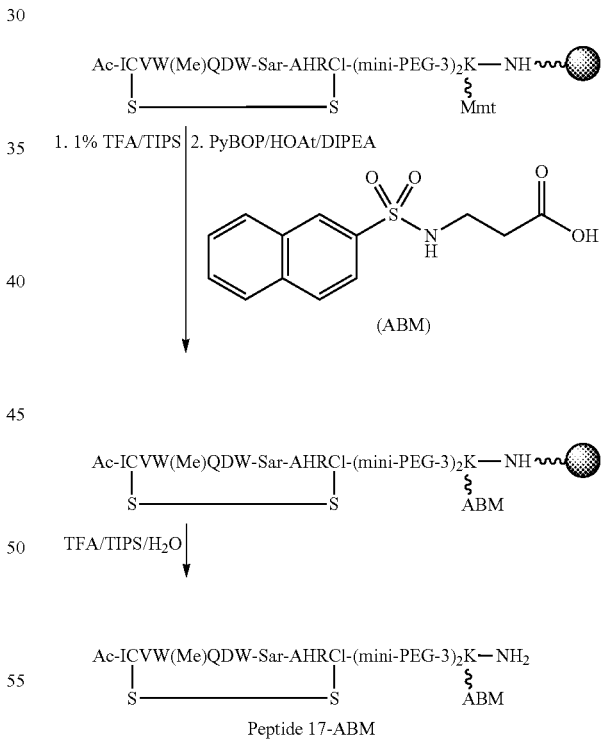

Synthesis of Peptide 17-ABP.

In solution azide-alkyne Huisgen cycloaddition was used for the conjugation, according to the reaction scheme below. The 2-azidoacetic acid was synthesized from 2-bromoacetic acid and sodium azide. It was then coupled to the C-terminal Lys side chain after formation of the disulfide bond on resin. Intermediates 2 and 3 were obtained in 12.7% and 12.3% yield, respectively, after cleavage and HPLC purification.

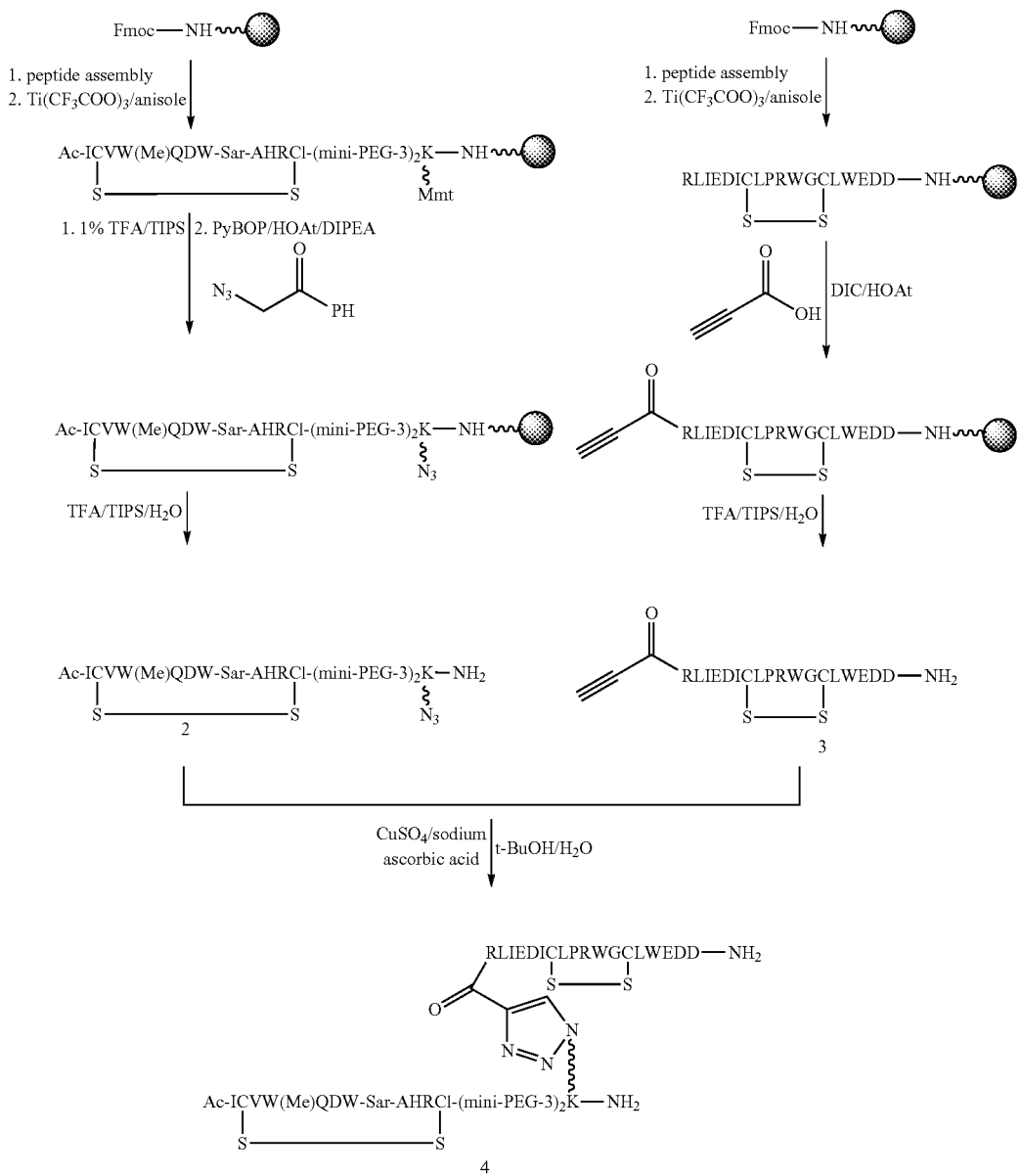

Peptide 17-ABP ("4" in the scheme above)

Three different solvent systems were compared for the azide-alkyne Huisgen cycloaddition. The best result was observed with t-BuOH/H$_2$O system, followed by ACN/H$_2$O system. No product was observed when DMF alone was used as solvent. The importance of tertiary base was also evaluated. No product was detected after 2 h without addition of excess TEA. Under optimized conditions, the reaction was clean and peptide 17-ABP was isolated in 50% yield after HPLC purification. The mass of the product was further confirmed by ESI-TOF ([MH]$^{4+}$ calc. 1131.78. found 1131.52).

Inhibition of Complement Activation.

The ability of peptide 17-ABM and peptide 17-ABP to inhibit classical pathway complement activation was evaluated by ELISA, using human serum. The results are shown in Table 2-1.

TABLE 2-1

Results of ELISA and SPR analyses of peptide 17 and ABP or ABM conjugates

| Peptide | IC$_{50}$ (nM, CP) | IC$_{50}$ (fold change*) | K$_{on}$ (10$^6$, M$^{-1}$·s$^{-1}$) | K$_{off}$ (10$^{-3}$, s$^{-1}$) | K$_D$ (nM) |
|---|---|---|---|---|---|
| Peptide 17 | 92 | 1 | 1.0 | 6.6 | 4.4 |
| Peptide 17-ABM | 137 | 0.67 | 1.2 | 5.6 | 4.7 |
| Peptide 17-ABP | 242 | 0.38 | 0.1 | 3.6 | 32 |

*Fold change is relative to peptide 17

Plasma Concentration in Baboons.

The plasma concentrations of peptide 17 and the ABP and ABM conjugates were determined using LC-MS/MS after an intravenous bolus injection into baboons. Peptide 17 showed a half-life of around 60 min. Peptide 17-ABM displayed a 5-fold improvement with a half-life of 5 h. The longest half-life of 21 h was observed for peptide 17-ABP, which was 21-fold greater than that of unconjugated peptide 17.

The present invention is not limited to the embodiments described and exemplified above, but is capable of variation and modification within the scope of the appended claims.

What is claimed:

1. A modified compstatin peptide (ICVVQDWGHHRCT (cyclic C2-C12); SEQ ID NO:1), in which the Gly at position 8 is N-methylated to constrain the backbone conformation of the peptide at that location, and comprising one or more additional modifications selected from:
   a) acetylated N-terminus;
   b) Ala instead of His at position 9 of the peptide;
   c) Trp or an analog of Trp instead of Val at position 4 of the peptide;
   d) halogenated Trp at position 7 of the peptide;
   e) Ile, Leu, Nle, N-methyl Thr or N-methyl Ile instead of Thr at position 13 of the peptide; and
   f) amidated C-terminus;
   wherein the peptide further comprises an albumin binding small molecule linked directly or indirectly thereto.

2. The modified compstatin peptide of claim 1, which includes Ala instead of His at position 9 of the peptide.

3. The modified compstatin peptide of claim 2, which includes Trp or an analog of Trp instead of Val at position 4 of the peptide.

4. The modified compstatin peptide of claim 3, wherein the analog of Trp at position 4 is 1-methyl Trp or 1-formyl Trp.

5. The modified compstatin peptide of claim 4, wherein the Trp at position 7 is a halogenated Trp.

6. The modified compstatin peptide of claim 1, wherein the N-terminus of the peptide is acetylated.

7. The modified compstatin peptide of claim 1, comprising Ile, Leu, Nle, N-methyl Thr or N-methyl Ile instead of Thr at position 13.

8. The modified compstatin peptide of claim 1, wherein the albumin binding small molecule is linked to a terminus of the peptide.

9. The modified compstatin peptide of claim 8, wherein the peptide is separated from the albumin binding small molecule by a spacer.

10. The modified compstatin peptide of claim 9, wherein the spacer is a polyethylene glycol molecule.

11. A pharmaceutical composition comprising the modified compstatin peptide of claim 1 and a pharmaceutically acceptable carrier.

12. A compstatin analog that binds C3 and inhibits complement activation with at least the same potency as compstatin, comprising a peptide having a sequence of SEQ ID NO:2, which is:

Xaa1a-Xaa1b-Cys-Val-Xaa2-Gln-Asp-Xaa3-Gly-Xaa4-His-Arg-Cys-Xaa5 (cyclic C2-C12) in which Gly at position 8 is N-methylated to constrain the backbone conformation at that location; wherein:

Xaa1a and Xaa1b together form position 1 of the peptide;

Xaa1a is missing or is Gly, provided Xaa1b is Ile;

Xaa1b is Ile, Val, Leu, Ac-Ile, Ac-Val, or Ac-Leu;

Xaa2 is Trp or an analog of Trp, wherein the analog of Trp has increased hydrophobic character as compared with Trp;

Xaa3 is Trp or an analog of Trp comprising a chemical modification to its indole ring wherein the chemical modification increases the hydrogen bond potential of the indole ring;

Xaa4 is His, Ala, Phe or Trp; and

Xaa5 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —NH$_2$;

wherein the compstatin analog further comprises an albumin binding small molecule linked directly or indirectly to the peptide.

13. The compstatin analog of claim 12, wherein Xaa1a is missing, Xaa1b is Ac-Ile, Xaa2 is 1-methyl-Trp or 1-formyl-Trp, Xaa3 is Trp, Xaa4 is Ala, and Xaa5 is Thr, Ile, Leu, Nle, N-methyl Thr or N-methyl Ile.

14. The compstatin analog of claim 13, wherein Xaa5 is Ile, N-methyl Thr or N-methyl Ile.

15. The compstatin analog of claim 12, which comprises any of SEQ ID NOS: 5, 7, 8, 9, 10 or 11.

16. The compstatin analog of claim 12, wherein the albumin binding small molecule is linked to a terminus of the peptide.

17. The compstatin analog of claim 16, wherein the peptide is separated from the albumin binding small molecule by a spacer.

18. The compstatin analog of claim 17, wherein the spacer is a polyethylene glycol molecule.

19. A pharmaceutical composition comprising the compstatin analog of claim 12 and a pharmaceutically acceptable carrier.

* * * * *

```
                            SEQUENCE LISTING

<160> NUMBER OF SEQ ID NOS: 14

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (8)..(8)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 2

Xaa Xaa Cys Val Xaa Gln Asp Xaa Gly Xaa His Arg Cys Xaa Xaa Xaa
1               5                   10                  15

<210> SEQ ID NO 3
<211> LENGTH: 13
<212> TYPE: PRT
<213> ORGANISM: Artificial sequence
<220> FEATURE:
<223> OTHER INFORMATION: synthetic sequence
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)

<400> SEQUENCE: 3

Ile Cys Val Tyr Gln Asp Trp Gly Ala His Arg Cys Thr
1               5                   10

<210> SEQ ID NO 4
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION

<400> SEQUENCE: 4

Ile Cys Val Trp Gln Asp Trp Gly Ala His Arg Cys Thr
1               5                   10

<210> SEQ ID NO 5
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 5

Ile Cys Val Trp Gln Asp Trp Gly Ala His Arg Cys Thr
1               5                   10

<210> SEQ ID NO 6
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
```

```
<221> NAME/KEY: MOD_RES
<222> LOCATION: (4)..(4)
<223> OTHER INFORMATION: METHYLATION

<400> SEQUENCE: 6

Ile Cys Val Trp Gln Asp Trp Gly Ala His Arg Cys Ile
1               5                   10

<210> SEQ ID NO 7
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 7

Ile Cys Val Trp Gln Asp Trp Gly Ala His Arg Cys Ile
1               5                   10

<210> SEQ ID NO 8
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 8

Ile Cys Val Trp Gln Asp Trp Gly Ala His Arg Cys Leu
1               5                   10

<210> SEQ ID NO 9
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
```

```
<220> FEATURE:
<221> NAME/KEY: MOD_RES
<222> LOCATION: (8)..(8)
<223> OTHER INFORMATION: METHYLATION
<220> FEATURE:
<221> NAME/KEY: VARIANT
<222> LOCATION: (13)..(13)
<223> OTHER INFORMATION: Xaa is norleucine

<400> SEQUENCE: 9

Ile Cys Val Trp Gln Asp Trp Gly Ala His Arg Cys Xaa
1               5                   10

<210> SEQ ID NO 10
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (13)..(13)
<223> OTHER INFORMATION: METHYLATION

<400> SEQUENCE: 10

Ile Cys Val Trp Gln Asp Trp Gly Ala His Arg Cys Thr
1               5                   10

<210> SEQ ID NO 11
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (13)..(13)
<223> OTHER INFORMATION: METHYLATION

<400> SEQUENCE: 11

Ile Cys Val Trp Gln Asp Trp Gly Ala His Arg Cys Ile
1               5                   10

<210> SEQ ID NO 12
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
```

```
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 12

Ile Cys Val Trp Gln Asp Trp Gly Ala His Arg Cys His
1               5                   10

<210> SEQ ID NO 13
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 13

Ile Cys Val Trp Gln Asp Trp Gly Ala His Arg Cys Phe
1               5                   10

<210> SEQ ID NO 14
<211> LENGTH: 18
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION

<400> SEQUENCE: 14

Arg Leu Ile Glu Asp Ile Cys Leu Pro Arg Trp Gly Cys Leu Trp Glu
1               5                   10                  15

Asp Asp
```